United States Patent [19]

Leight

[11] Patent Number: 5,322,185

[45] Date of Patent: Jun. 21, 1994

[54] EARPLUG DISPENSER SYSTEM

[76] Inventor: Howard S. Leight, 1330 Colorado Ave., Santa Monica, Calif. 90404

[21] Appl. No.: 54,555

[22] Filed: Apr. 27, 1993

[51] Int. Cl.⁵ .............................................. G07F 11/54
[52] U.S. Cl. ........................................ 221/2; 221/1; 221/22; 221/186; 221/197; 221/203; 221/258; 221/265; 221/277; 221/281; 221/287
[58] Field of Search ................ 221/1, 2, 13, 14, 22, 221/64, 65, 89, 90, 174, 186, 196, 197, 200, 203, 258, 264, 265, 277, 281, 282, 286, 287; 141/1, 2, 18, 21, 98, 114, 363, 364

[56] References Cited

U.S. PATENT DOCUMENTS

| | | | |
|---|---|---|---|
| 1,321,385 | 11/1919 | Millard | 221/265 X |
| 1,982,273 | 11/1934 | Vogel et al. | 221/281 X |
| 2,330,256 | 9/1943 | Ashton | 221/265 |
| 2,649,994 | 8/1953 | Lewis et al. | 221/265 |
| 2,664,223 | 12/1953 | Dobkin | 221/265 |
| 2,880,906 | 4/1959 | Probasco | 221/265 X |
| 3,128,011 | 4/1964 | Bleiman | 221/265 X |
| 4,555,624 | 11/1985 | Steffen | 221/2 X |

Primary Examiner—Robert P. Olszewski
Assistant Examiner—Dean A. Reichard
Attorney, Agent, or Firm—Arthur Freilich; Robert D. Hornbaker; Leon D. Rosen

[57] ABSTRACT

An apparatus is described which can receive a large number of earplugs from a box and dispense one or two of them at a time to a worker. The apparatus includes a wheel (22, FIG. 1) which is rotatable on a frame (12) and which has holes (24) that move in a circular path and that can each receive a single earplug (16). As each hole moves over a dispense passage 18, the earplug in the hole can fall out, and be dispensed. A barrier (42, FIG. 2) lying above the wheel, prevents an earplug from falling into a hole that lies at the passage. The barrier covers only one side (52) of the path (32) of the holes, to allow a deformed earplug to move along the other, uncovered side (54) of the path. The wheel has a narrow slot (80) extending from each hole to the periphery, so a tool can be projected through a frame opening (84) and through the slot to dislodge an earplug stuck in a wheel hole.

12 Claims, 5 Drawing Sheets

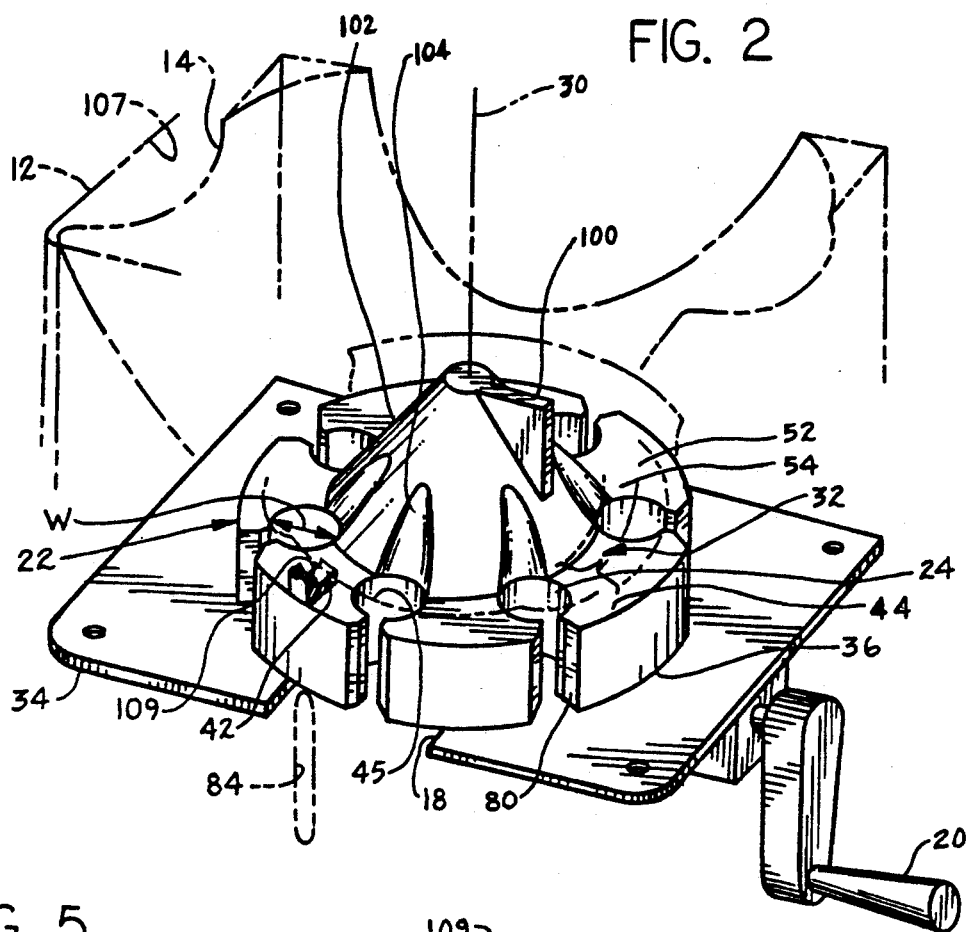
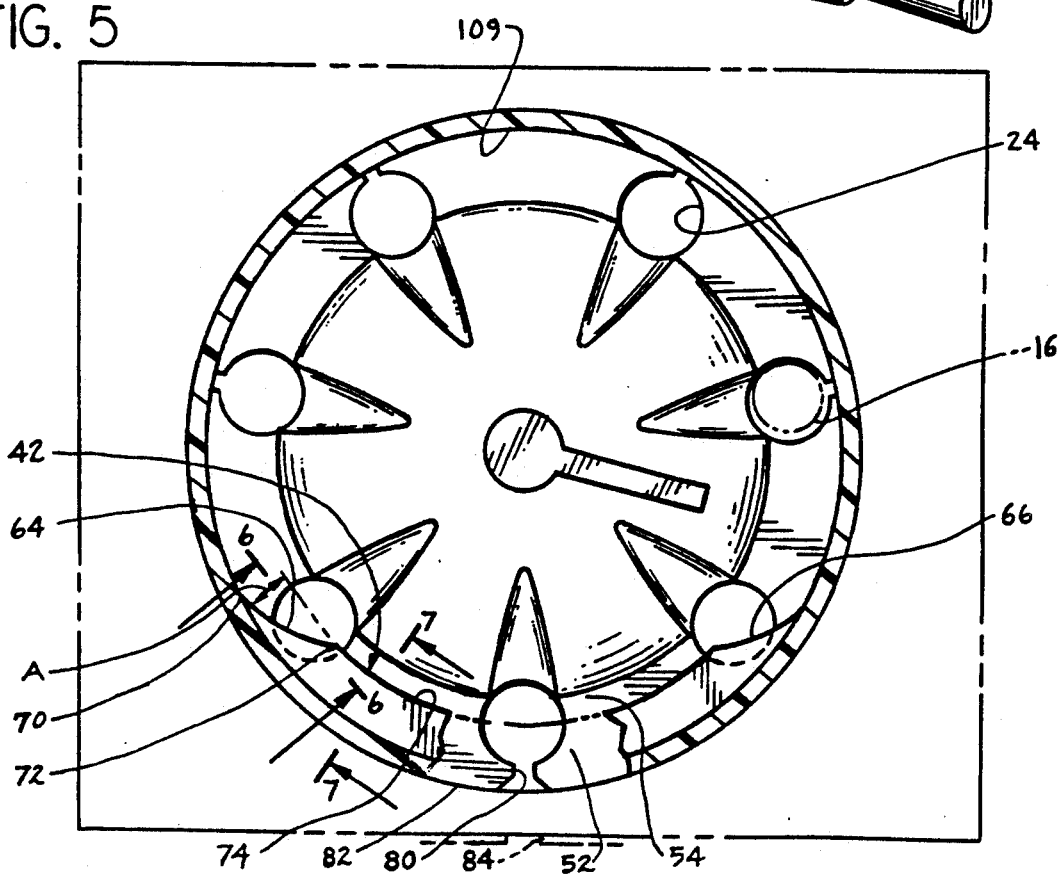

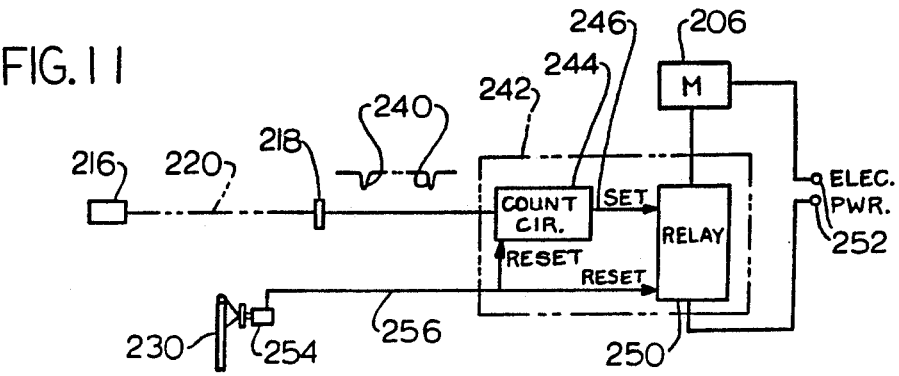
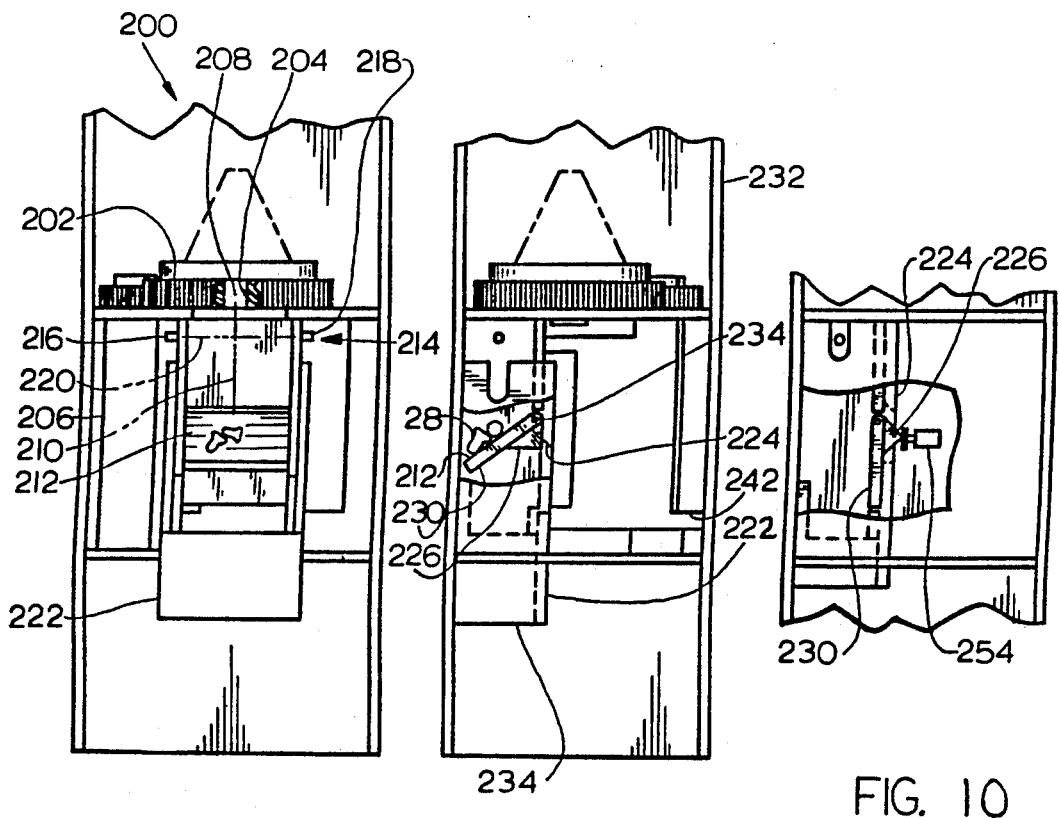

EARPLUG DISPENSER SYSTEM

BACKGROUND OF THE INVENTION

Large numbers of disposable earplugs are used in industrial plants, with each worker taking a pair of earplugs at a time. In some situations, a large box of earplugs is opened, and workers place their hands in the box to pick up a pair of earplugs. If a worker picks up more than two earplugs, he may simply throw the additional ones away. Furthermore, if a worker has dirty hands, he may leave dirt on other earplugs and other workers will not want to use them. Another approach is to place each pair of earplugs in a separate plastic bag. The disposable earplugs may cost only several pennies apiece, so the need to place pairs of them in separate packages can add substantially to the cost of a box of several hundred earplugs. A dispenser which enabled "loose" earplugs to be used, with minimal wastage by workers taking more than two earplugs at a time and which avoided soiling of earplugs as a result of handling by workers, would be of considerable value.

SUMMARY OF THE INVENTION

In accordance with one embodiment of the present invention, an earplug dispensing apparatus is provided for facilitating the dispensing of earplugs while avoiding soiling or loss of earplugs prior to dispensing. The apparatus includes a wheel rotatable on a frame and having holes that each can hold a single earplug. As the wheel turns, earplugs drop from a bin or hopper into the wheel holes. The wheel holes carry individual earplugs to a dispense location at which each earplug drops out of a hole. A barrier lies above an approach to the dispense location, to prevent an earplug from falling into the wheel hole thereat as well as to sweep away a second earplug that initially lies partially in the hole.

The barrier can lie above only one side of the hole path, to allow a deformed earplug to pass along the unobstructed other side without being cut. The barrier ends preferably extend in a smooth transition angled less than 45° to the hole path, to gently push a trapped earplug to said other side. The wheel preferably has narrow slots, each extending radially from its periphery to each hole. If an earplug is jammed in a hole, a person inserts a tool through an opening in the frame and through a slot to dislodge the jammed earplug.

The novel features of the invention are set forth with particularity in the appended claims. The invention will be best understood from the following description when read in conjunction with the accompanying drawings.

BRIEF DESCRIPTION OF THE DRAWINGS

FIG. 2 is an isometric view of the dispensing mechanism of the dispenser of FIG. 1, with the hopper shown in phantom lines.

FIG. 5 is a partially sectional plan view of the dispensing mechanism of FIG. 2.

FIG. 8 is a partial front elevation view of an earplug dispenser constructed in accordance with another embodiment of the invention, wherein the wheel is turned by an electric motor and holds a pair of earplugs for rapid removal by a workman.

FIG. 9 is a side view of the dispenser of FIG. 8.

FIG. 10 is a view similar to that of FIG. 9, but with the retainer arm lowered.

FIG. 11 is a block diagram of a circuit of the dispenser of FIG. 8.

DESCRIPTION OF THE PREFERRED EMBODIMENTS

Figure 1:
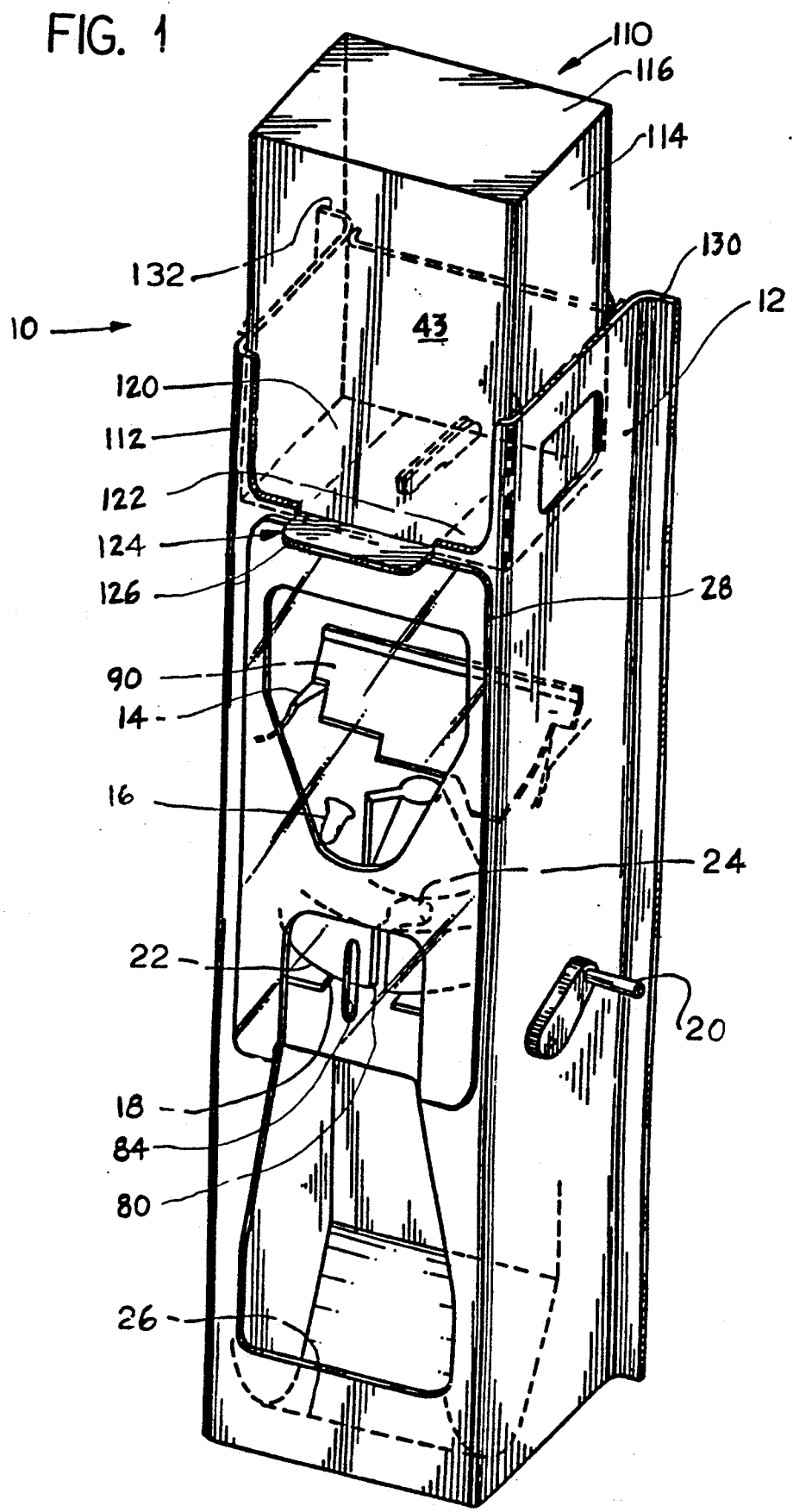
FIG. 1 is an isometric view of an earplug dispenser of the present invention.

FIG. 1 illustrates an earplug dispenser 10 which includes a frame 12 that forms a bin or hopper (which may or may not be tapered) 14. The hopper 14 holds a large number of earplugs 16 such as several hundred of them when filled. The earplugs are dispensed one at a time through a dispense passage 18. A worker turns a crank 20 to turn a wheel 22 that lies within the frame. The wheel has a plurality of holes 24 that are each large enough to hold a single one of the earplugs. As the wheel turns, each hole 24, which generally has received a single earplug, passes to a dispense location which lies over the dispense passage 18. The earplug in the hole drops out of the hole into the dispense passage, and into the waiting hand of the worker or into a holding station 26. The frame is constructed of opaque material, except for a transparent plate 28 that allows viewing of the dispensing mechanism.

Disposable earplugs are used in large numbers in industry. At the beginning of the workday, and possibly after lunch and each work break, a worker may take another pair of earplugs which he will later throw away. Worker's hands often contain considerable dirt or grease, and if a worker dips his hand into a box of earplugs to pull out two, he may soil adjacent earplugs. There are disadvantages to packaging each pair of earplugs in a separate bag, in that the bag adds to the cost of the pair of earplugs, and may be annoying for the worker to open. The present dispenser allows each worker to obtain a pair of earplugs from a "loose" pile of them, while minimizing the possibility of a worker with dirty hands soiling other earplugs, and while avoiding wastage of earplugs that can occur when a worker picks up more than two earplugs and has to throw away the extra ones.

As shown in FIG. 2, the wheel 22 is rotatably mounted on the frame 12 about an axis 30. The wheel holes 24 are equally spaced from the axis of rotation, and move in a circular path 32 as the wheel turns. The holes are of cylindrical shape, and the path 32 has the width W of the holes. A retainer 34, which is part of the frame and is in the form of a plate, lies adjacent to the lower surface 36 of the wheel to prevent the earplugs from falling out of the wheel before they reach the dispense location. The retainer lies under the entire circular path of the holes, except for a cutout where it forms part of the dispense passage 18. A barrier 42 lies immediately above the upwardly-facing top surface 44 of the wheel, to sweep away any second earplug that lies partially in one of the holes above a first earplug that lies fully in the hole. The barrier also blocks the space above the dispense passage 18, to prevent a second earplug from falling into one of the holes as an earplug falls out of the hole at a dispense location 45 which lies above the dispense passage. Of course, the exact location where the earplug drops out of a hole varies slightly, depending on the direction of wheel rotation, etc.

Figure 6:
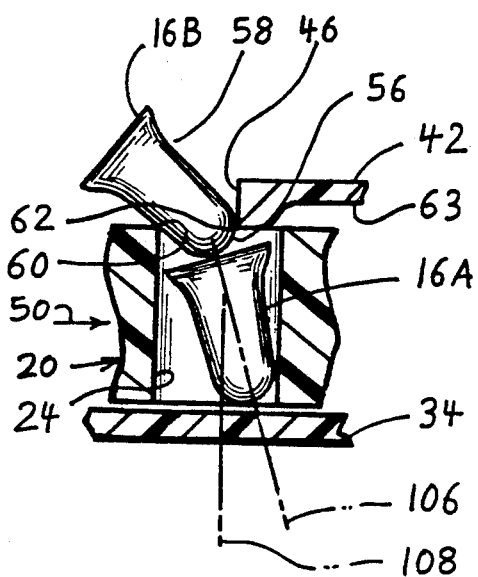
FIG. 6 is a sectional view taken on line 6—6 of FIG. 5, showing how the barrier rejects an extra earplug from a wheel hole.

FIG. 6 shows how the leading edge 46 of the barrier 42 can sweep away a second earplug 16B which initially lies partially in a hole 24 above a first earplug 16A. It is assumed that the wheel 22 is moving in the direction of arrow 50. The earplug may be of the type described in U.S. Pat. No. 4,774,938, wherein the earplug is of a soft foam material that is easily deformed but slowly returns to its original configuration.

Figure 7:
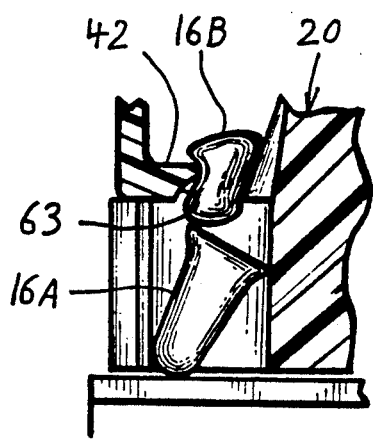
FIG. 7 is a sectional view taken on the line 7—7 of FIG. 5, showing how the barrier accommodates a trapped earplug.

As shown in FIG. 5, the barrier 42 lies above only a first side 52 of the hole path 32, while leaving the space immediately above the second side 54 of the hole path unobstructed. It is possible for a second earplug 16B (FIG. 6) to lie with its lower part 56 trapped in a wheel hole so it is forced to move along the hole path as the wheel turns. In that case, the upper part 58 of that earplug can be accommodated along the second side 54 of the path. Without the uncovered second path side, such a trapped earplug might be squeezed between corners 60, 62 of the wheel hole and of the barrier, and be cut or jam the dispenser. FIG. 7 shows the second earplug 16B with its lower end in the hole, and its middle only temporarily deformed and moving along the second side 54 of the path. The barrier has a recess 63 in its lower surface, except at its ends. The recess opens toward the second path side to minimize deformation of a trapped earplug.

The ends 64, 66 (FIG. 5) of the barrier are smoothly tapered from the extreme uppath location 70 where the barrier starts to cross the hole path to the downpath location 72 from which the middle barrier edge 74 extends parallel to the hole path. In FIG. 5, the middle barrier edge 74 extends along the centerline 76 of the path. The average taper angle A of each barrier end relative to the path centerline 76 is preferably no more than 60°, more preferably no more than 45°, and most preferably no more than 30°. The moderate taper angle causes a trapped earplug to be deflected to the second side 54 of the path (or beyond), rather than be stopped at the barrier end and possibly be cut. The term "smooth taper" means that the barrier end is devoid of protrusions, recesses, or the like where an earplug could be stopped and then cut by the moving wheel.

The wheel has a plurality of largely radially extending slots 80, each extending from the periphery 82 of the wheel to one of the holes 24. Each slot is narrower than the width, or diameter, of the hole (as seen in a plan view), and narrower than an earplug to prevent an earplug from passing through the slot. The slot, at its narrowest, is preferably less than half the width of a wheel hole. If an earplug should become jammed in a hole, a person can project a tool, such as a key or screwdriver blade, through an opening 84 in the frame and through a slot 80, to move the earplug.

Figures 3, 4:
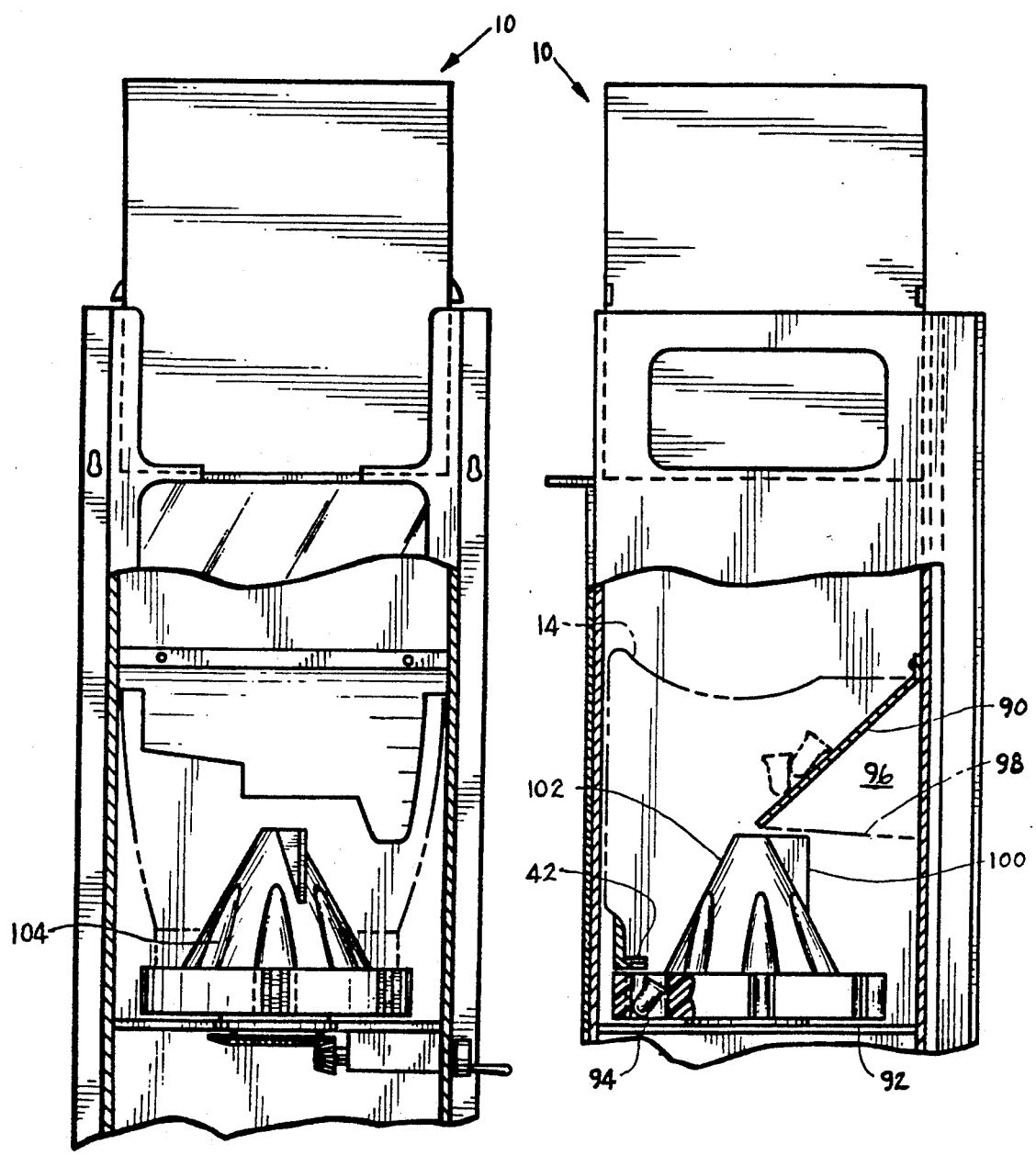
FIG. 3 is a partial front view, partly in section, of the dispenser of FIG. 1.
FIG. 4 is a partially sectional side view of the dispenser of FIG. 1.

The frame preferably includes an inclined wall 90 (FIG. 4) lying above a first portion 92 of the circular path of the wheel holes, but not above a second portion 94. If the hopper 14 is nearly completely filled with earplugs, the weight of the earplugs can tend to "jam" the earplugs together. Such "jamming" can prevent earplugs from falling into the wheel holes. The inclined wall 90 provides a jam-protected region 96 lying under the inclined wall, where earplugs are largely protected from jamming by the weight of a large number of earplugs above them. The earplugs stack up only to a height indicated at 98, which results in the jam-protected region 96. The wheel includes a stir arm 100 that passes into and out of the jam-protected region 96 and a region above the second portion 94 of the path, to move the earplugs and avoid jamming.

The wheel 22 (FIG. 2) includes an upward projection 102 lying radially within the path of the wheel holes. The projection forms a plurality of inclined guideways 104 that are each positioned to guide an earplug in downwardly inclined motion into a corresponding one of the wheel holes 24. This aids in filling each hole with an earplug, by helping to align the earplug so the axis 106 (FIG. 6) of the earplug tends to align with the vertical axis 108 of the hole.

The hopper 14 (FIG. 2) forms a transition from a substantially rectangular frame upper portion 107 to a circular lower hopper end 109 shown in FIG. 5.

Whenever the supply of earplugs in the hopper 14 (FIG. 1) runs low, a new batch of earplugs is installed by dumping earplugs held in a box 110 into the frame 12. Applicant facilitates the transfer of earplugs from the box 110 to the frame hopper 14, by constructing the frame top 112 so it can receive the box 110, and by constructing the box so it can be opened after full installation in the frame.

The box 110 is of largely conventional construction, with four side walls 114, a top wall 116, and a bottom wall formed by a pair of flaps 120, 122. A release device 124 holds the flaps together. When the release device is pulled out, by grasping a handle 126 and pulling, the flaps are free to pivot down so the earplugs can fall out.

The particular earplug dispenser 10 shown in FIG. 1, has a pair of flanges 130, 132 to enable the frame to be mounted on a wall. The relative simplicity of the dispenser enables it to be constructed at moderate cost and operate reliably.

FIGS. 8-11 illustrate another earplug dispenser 200 wherein the wheel 202 which has holes 204 for holding earplugs, is driven by an electric motor 206. As the wheel turns, earplugs in a hole such as 204, come to a dispense location 208 where the earplugs drop along a predetermined path 210 to an earplug holding station 212. A sensor device 214 which comprises a light beam source 216 and a light beam detector 218 lie on opposite sides of the dispense path. When an earplug falls along the dispense path 210, the earplug interrupts a light beam 220, which is detected by the photodetector 218. After the light beam 220 has been interrupted two times, to indicate that two earplugs have been dispensed, the motor 206 is no longer energized. However, when a person removes the earplugs from the holding station 212, a control senses this and reenergizes the motor to again dispense two earplugs.

The particular mechanism for removing the earplugs includes a sleeve 222 (FIG. 9) which has a cam 224 that abuts a cam follower 226 on a retainer arm 230. The retainer arm is pivotally mounted on the frame 232, at a pivot location 234. When the sleeve 222 is lifted, it no longer prevents movement of the cam follower, and the retainer arm 230 moves down and allows the earplugs 16 at the holding station 212 to fall down through the sleeve and be caught in the hand of the person who is pushing upwardly on the bottom 234 of the sleeve. FIG. 10 shows the retainer arm 230 in the down position.

As shown in FIG. 11, every time an earplug interrupts the light beam 220, the photodetector generates a pulse 240. A control 242 includes a count circuit 244 which delivers a signal over line 246 after two pulses are received from the photodetector 218. The signal on line 246 sets a relay 250, to open the relay contacts. This prevents electricity from terminals 252 connected to an electrical power source, from energizing the motor. A holder detector 254, such as a switch, detects lowering of the retainer arm 230, and upon detecting such lowering delivers a signal over line 256 to the counting circuit 244 to reset it, and to the relay 250 to reset the relay. The reset relay is closed, and allows power to flow to the motor 206 to energize it. The motor turns the wheel until two more earplugs have been dispensed.

Thus, the invention provides an earplug dispenser which facilitates the dispensing of earplugs. The dispenser includes a movable earplug-holding device which can be in the form of a belt or chain, but which is preferably a rotatable wheel having a plurality of holes that are each capable of holding a single earplug. The holes move in a circular hole path as the wheel turns, to bring each hole over a dispense passage of the dispenser frame, where an earplug drops out of a hole. A retainer lies immediately below the wheel, but not at the dispense passage, and a barrier lies immediately (less than the earplug width) above the wheel at the dispense location. The barrier preferably covers only one side of the hole path, and preferably has a smoothly tapered end. The wheel has slots leading to the holes to facilitate removal of a jammed earplug. The wheel has an upward projection forming inclined guideways that guide earplugs into the holes. The wheel has a stir arm that moves earplugs from a region where earplugs can jam to a jam-protected region lying under an inclined hopper wall. A motor-powered dispenser can be used, which detects the dispensing of an earplug and which energizes the motor to continue turning the wheel until the sensor device detects the dispensing of two earplugs to a holding station.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. An earplug dispenser which includes a frame that forms a dispense passage, an earplug-holding device that is movable on said frame and that has a plurality of holes that move in a hole path past a dispense location above said dispense passage where earplugs can fall out of said holes into said passage, characterized by:
    a barrier which prevents an earplug from falling into one of said holes at said dispense location, said barrier having a lower surface lying above one side of said hole path, and said barrier has a recess in its lower surface which opens to the other side of said path.

2. The earplug dispenser described in claim 1 wherein:
    said device rotates about an axis, said barrier has an end with a radially inner edge which extends, as seen in a plan view, smoothly at an angle of no more than 60° to said path, and said barrier has a middle which extends substantially along a circle centered on said axis.

3. An earplug dispenser which includes a frame that forms a dispense passage, a wheel rotatably mounted about an axis on said frame and having a plurality of holes that move in a circular path past a dispense location above said dispense passage where earplugs can fall out of said holes into said passage, characterized by:
    said wheel has a periphery and has a plurality of slots each extending radially from said wheel periphery to one of said holes, to facilitate removal of earplugs lying in said holes, each of said slots having a narrowest width that is less than the width of one of said holes as seen in a view taken along said axis.

4. The earplug dispenser described in claim 3 wherein:
    said frame has an opening which lies at about the same height as said wheel and which can pass a tool from outside said frame into one of said wheel slots to dislodge a trapped earplug.

5. The earplug dispenser described in claim 3 including:
    a barrier which lies immediately above said wheel holes to block downward movement of an earplug into a hole lying at said dispense location, said barrier having an end lying along said hole path, with said end extending smoothly at an average angle of no more than 45° to said path and said barrier having a middle with a radially inner edge extending largely along a circle centered on said axis.

6. The earplug dispenser described in claim 3 wherein:
    said frame forms a hopper with an inclined wall lying above a first portion of said path but not above a second portion of said path, to leave a jam-protected region below said inclined wall which avoids the jamming together of earplugs above said path;
    said earplug-holding device has a stir arm that projects into a region above said path but below at least part of said inclined wall, to move earplugs from a region above said second path portion into said jam-protected region to avoid jamming of earplugs lying above said second portion of said path.

7. The earplug dispenser described in claim 3 wherein:
    said wheel includes a largely conical upward projection lying radially within the path of said holes, said projection forming a plurality of inclined grooves each positioned to guide an earplug into a corresponding one of said holes, with each groove having an upper portion that is tapered in width to be progressively wider at progressively lower locations therealong.

8. A method for dispensing one at a time, easily deformable earplugs of a predetermined earplug size, comprising:
    rotatably mounting a wheel about an axis in a frame, where said wheel has a plurality of holes lying on an imaginary circle centered on said axis, so said holes move along a circular path as said wheel rotates, with each of said holes being large enough to hold only a single complete one of said earplugs, and with said path having radially inner and outer sides;
    establishing a multiplicity of said earplugs above said wheel;
    establishing a barrier immediately above a part of said path to prevent earplugs from dropping through said barrier into wheel holes lying at said part of said path, while allowing earplugs to fall into said holes at other locations along said path;

establishing a dispense passage immediately below said part of said path to lie under said barrier while blocking regions lying immediately under portions of said path that are spaced from said passage;

rotating said wheel, while allowing earplugs to fall into said wheel holes at locations away from barrier, and allowing one earplug at a time that lies in one of said wheel holes to fall out through said passage;

said step of establishing a barrier includes establishing a barrier above only one of said sides of said path part but not above the other side and moving at least a portion of an earplug in a partially deformed state along said other side of said path part.

9. The method described in claim 8 including:

constructing said wheel with a periphery and with a plurality of slots each extending radially between said periphery and one of said holes, and constructing said frame with an opening that is largely in line with said wheel periphery;

loosening an earplug that is stuck in one of said holes by projecting a tool through said frame opening and through one of said slots into said one of said holes.

10. An earplug dispenser which includes a frame that forms a dispense passage, an earplug-holding device that is movable on said frame and that has a plurality of holes that move in a hole path past a location above said dispense passage where earplugs can fall out of said holes into said passage, characterized by:

said frame forms a hopper with an inclined wall lying above a first length of said path but not above a second length of said path, to leave a jam-protected region below said inclined wall which avoids the jamming together of earplugs above said path;

said earplug-holding device has a stir arm that projects into a region above said path but below at least part of said inclined wall, to move earplugs from a region above said second path length into said jam-protected region to avoid jamming of earplugs lying above said second length of said path.

11. An earplug dispenser which includes a frame that forms a dispense passage, an earplug-holding device that is movable on said frame and that dispenses individual earplugs along a dispense passage, characterized by:

an earplug holding station lying along said dispense passage;

a motor coupled to said earplug-holding device to move it;

a sensor device which detects that an earplug has dropped along said dispense passage;

a control coupled to said sensor device and said motor, said control constructed to energize said motor until said sensor device senses that a predetermined number of earplugs have dropped along said passage, and to then stop energizing said motor.

12. The dispenser described in claim 11 wherein:

said control is constructed to energize said motor until said sensor device senses that two earplugs have dropped along said passage.

* * * * *